US009883932B2

(12) United States Patent
Trompen et al.

(10) Patent No.: US 9,883,932 B2
(45) Date of Patent: Feb. 6, 2018

(54) TRANSDERMAL DISPENSING APPARATUS AND METHODS

(71) Applicants: Mick A. Trompen, Westfield, IN (US); Gregory A. Lyon, Indianapolis, IN (US); Terrence Patrick Clark, Cottage Grove, WI (US); Garret Conrad Newbound, Carmel, IN (US)

(72) Inventors: Mick A. Trompen, Westfield, IN (US); Gregory A. Lyon, Indianapolis, IN (US); Terrence Patrick Clark, Cottage Grove, WI (US); Garret Conrad Newbound, Carmel, IN (US)

(73) Assignees: Aircom Manufacturing, Inc., Indianapolis, IN (US); Eli Lilly and Company, Greenfield, IN (US)

( * ) Notice: Subject to any disclaimer, the term of this patent is extended or adjusted under 35 U.S.C. 154(b) by 123 days.

(21) Appl. No.: 14/618,993

(22) Filed: Feb. 10, 2015

(65) Prior Publication Data

US 2015/0150665 A1 Jun. 4, 2015

Related U.S. Application Data

(63) Continuation of application No. 12/581,658, filed on Oct. 19, 2009, now abandoned.

(51) Int. Cl.

*A61D 7/00* (2006.01)
*A01K 13/00* (2006.01)
*A61M 35/00* (2006.01)

(52) U.S. Cl.

CPC .............. *A61D 7/00* (2013.01); *A01K 13/003* (2013.01); *A61M 35/00* (2013.01); *A61M 35/003* (2013.01); *Y10T 29/49826* (2015.01)

(58) Field of Classification Search

CPC ........ A61D 7/00; A01K 13/003; A45D 24/22; A45D 24/26
USPC ................. 119/603, 650; 132/115, 112–114; 604/94.01, 289–290, 310–311
See application file for complete search history.

(56) References Cited

U.S. PATENT DOCUMENTS

| | | | |
|---|---|---|---|
| 655,816 | A | 8/1900 | Vogel |
| 676,379 | A | 6/1901 | Young |
| 678,044 | A | 7/1901 | Myers |
| 1,105,934 | A | 8/1914 | Stevens |

(Continued)

FOREIGN PATENT DOCUMENTS

| | | | |
|---|---|---|---|
| WO | WO8809632 | * | 12/1988 |
| WO | WO-94/20379 | A1 | 9/1994 |

OTHER PUBLICATIONS

International Search Report and Written Opinion, PCT/US2010/053206, dated Feb. 17, 2011.

*Primary Examiner* — Paula L. Craig
(74) *Attorney, Agent, or Firm* — Bose McKinney & Evans LLP

(57) ABSTRACT

An applicator for dispensing a therapeutic agent to an animal including a housing including first and second sections coupled together, the first and second sections defining a channel therebetween that includes at least one outlet; a hub integral with the first section and extending therefrom, the hub defining a conduit; and a bent path connecting the conduit to the channel. In accordance with this embodiment, the conduit, the bent path and the channel are fluidly connected.

16 Claims, 9 Drawing Sheets

(56) References Cited

U.S. PATENT DOCUMENTS

| | | | | | |
|---|---|---|---|---|---|
| 1,187,847 | A | * | 6/1916 | Landre | A45D 19/02 132/112 |
| 1,209,424 | A | * | 12/1916 | Foley | A45D 24/24 132/113 |
| 1,362,780 | A | | 12/1920 | Chapman | |
| 1,413,320 | A | | 4/1922 | Charles | |
| 1,462,400 | A | | 7/1923 | Warren | |
| 1,525,106 | A | | 2/1925 | Smythe | |
| 1,525,955 | A | | 2/1925 | Sanders | |
| 1,574,418 | A | | 2/1926 | Coviello | |
| 1,823,850 | A | | 9/1931 | Marshall | |
| 1,829,021 | A | | 10/1931 | Sinclair | |
| 1,991,345 | A | | 2/1935 | Durand | |
| 2,139,904 | A | | 12/1938 | Merrill | |
| 2,270,530 | A | | 1/1942 | Kirchenbaum | |
| 2,295,746 | A | | 9/1942 | Metzler | |
| 2,376,065 | A | | 5/1945 | Kuszyk | |
| 2,381,048 | A | | 8/1945 | Habostad | |
| 2,470,297 | A | | 5/1949 | Fields | |
| 2,532,001 | A | | 11/1950 | Williams | |
| 2,604,102 | A | | 7/1952 | Laing | |
| 2,617,431 | A | | 11/1952 | Gaspari | |
| 2,660,251 | A | | 11/1953 | Birosh | |
| 2,694,401 | A | | 11/1954 | Francis | |
| 2,790,190 | A | | 4/1957 | Mastrandrea | |
| 2,900,651 | A | | 8/1959 | Powell | |
| 2,943,602 | A | | 7/1960 | Rundle | |
| 3,066,669 | A | | 12/1962 | DeMelfy | |
| 3,137,305 | A | | 6/1964 | Jones | |
| 3,353,721 | A | | 11/1967 | Love | |
| 3,457,928 | A | | 7/1969 | Kurshneoff | |
| 3,477,447 | A | | 11/1969 | Eldredge | |
| 3,520,311 | A | | 7/1970 | Karfo et al. | |
| 3,874,380 | A | | 4/1975 | Baum | |
| 3,961,635 | A | | 6/1976 | Miya | |
| 3,964,501 | A | | 6/1976 | Matchett | |
| 4,044,724 | A | | 8/1977 | Merchill | |
| 4,055,195 | A | | 10/1977 | Moses | |
| 4,090,522 | A | | 5/1978 | Donley et al. | |
| 4,183,328 | A | | 1/1980 | Lawrence | |
| 4,213,423 | A | | 7/1980 | Bryan et al. | |
| 4,213,473 | A | | 7/1980 | Dawson | |
| 4,237,822 | A | | 12/1980 | Kaiser, Jr. | |
| 4,294,270 | A | | 10/1981 | Cochran | |
| 4,495,958 | A | | 1/1985 | Roeder | |
| 4,543,913 | A | | 10/1985 | Wilkeson | |
| 4,564,360 | A | | 1/1986 | Young et al. | |
| 4,605,026 | A | | 8/1986 | Nolin | |
| 4,629,455 | A | * | 12/1986 | Kanno | A61M 5/344 285/332 |
| 4,631,055 | A | | 12/1986 | Redl et al. | |
| 4,735,616 | A | | 4/1988 | Eibl et al. | |
| 4,799,456 | A | | 1/1989 | Young | |
| 4,865,482 | A | | 9/1989 | Van Landingham | |
| 4,867,183 | A | | 9/1989 | Busch et al. | |
| 4,913,172 | A | | 4/1990 | Chou | |
| 4,922,859 | A | | 5/1990 | Durell et al. | |
| 4,958,596 | A | | 9/1990 | Belan | |
| 5,027,747 | A | | 7/1991 | Talley | |
| 5,054,504 | A | | 10/1991 | Winrow | |
| 5,092,854 | A | * | 3/1992 | Black | A61M 3/0279 604/243 |
| 5,104,375 | A | | 4/1992 | Wolf et al. | |
| 5,116,315 | A | | 5/1992 | Capozzi et al. | |
| D336,043 | S | | 6/1993 | Provencio | |
| 5,297,882 | A | | 3/1994 | Kornides | |
| 5,307,825 | A | | 5/1994 | Smith | |
| 5,325,878 | A | | 7/1994 | McKay | |
| 5,339,839 | A | | 8/1994 | Forcelledo et al. | |
| 5,361,947 | A | | 11/1994 | Lifshey | |
| 5,425,480 | A | | 6/1995 | Rabenau et al. | |
| 5,445,523 | A | | 8/1995 | Fischer et al. | |
| 5,474,540 | A | | 12/1995 | Miller et al. | |
| 5,482,058 | A | | 1/1996 | Garconnet | |
| 5,555,899 | A | | 9/1996 | Foreman | |
| 5,582,596 | A | | 12/1996 | Fukunaga et al. | |
| 5,803,093 | A | | 9/1998 | Romano | |
| 5,810,004 | A | | 9/1998 | Ohki et al. | |
| 5,823,145 | A | | 10/1998 | Hingiss | |
| 5,845,651 | A | * | 12/1998 | de Nervo | A45D 19/02 132/114 |
| 5,899,202 | A | | 5/1999 | Ohki et al. | |
| 5,906,198 | A | | 5/1999 | Flickinger | |
| 5,961,489 | A | | 10/1999 | Hirota | |
| 5,989,217 | A | | 11/1999 | Ohki et al. | |
| 6,024,052 | A | | 2/2000 | Efaw | |
| 6,035,806 | A | | 3/2000 | Lorenzo | |
| D428,525 | S | | 7/2000 | Gazzo | |
| 6,132,396 | A | | 10/2000 | Antanavich et al. | |
| 6,260,557 | B1 | | 7/2001 | Yarbrough | |
| 6,261,275 | B1 | | 7/2001 | Hayes | |
| 6,367,421 | B1 | | 4/2002 | Deacon | |
| 6,471,670 | B1 | | 10/2002 | Enrenfels et al. | |
| 6,482,187 | B1 | | 11/2002 | Gibbs | |
| 6,516,795 | B1 | | 2/2003 | Bougamont et al. | |
| 6,527,750 | B1 | | 3/2003 | Frandsen | |
| 6,539,949 | B2 | | 4/2003 | Christensen | |
| 6,684,887 | B2 | | 2/2004 | Alexander | |
| 6,732,888 | B1 | | 5/2004 | Smiley et al. | |
| 6,733,472 | B1 | | 5/2004 | Epstein et al. | |
| 6,736,802 | B1 | | 5/2004 | Recanati | |
| 6,877,924 | B1 | | 4/2005 | Mears et al. | |
| 6,962,158 | B1 | | 11/2005 | Anguelo | |
| 6,976,495 | B2 | | 12/2005 | Vena et al. | |
| 7,000,618 | B2 | | 2/2006 | Dovergne et al. | |
| D521,863 | S | | 5/2006 | Davis et al. | |
| 7,077,146 | B1 | | 7/2006 | Eckerson | |
| 7,204,829 | B2 | | 4/2007 | Hung et al. | |
| D558,920 | S | | 1/2008 | Sheppard et al. | |
| 7,331,352 | B2 | | 2/2008 | Ramet | |
| 7,409,957 | B2 | | 8/2008 | Abergel | |
| 7,435,029 | B1 | | 10/2008 | Marini | |
| 7,798,154 | B2 | | 9/2010 | De Laforcade | |
| 7,934,512 | B2 | | 5/2011 | Spagnuolo | |
| 8,118,036 | B2 | | 2/2012 | Wang et al. | |
| 8,603,984 | B2 | * | 12/2013 | Newbound | A61K 9/0019 514/18.4 |
| 8,613,738 | B2 | * | 12/2013 | Mantell | A61M 13/003 285/332.3 |
| 8,967,156 | B1 | * | 3/2015 | Skidmore | A45D 19/0008 132/112 |
| 2002/0092538 | A1 | * | 7/2002 | Thiebaut | A45D 19/02 132/116 |
| 2002/0096184 | A1 | | 7/2002 | Elmer et al. | |
| 2003/0209251 | A1 | | 11/2003 | Alexander | |
| 2005/0028833 | A1 | | 2/2005 | Vena et al. | |
| 2005/0184091 | A1 | * | 8/2005 | Abergel | A45D 19/02 222/145.5 |
| 2006/0032458 | A1 | | 2/2006 | Hutchinson et al. | |
| 2006/0095017 | A1 | | 5/2006 | Hung et al. | |
| 2007/0068545 | A1 | | 3/2007 | Dallianis et al. | |
| 2008/0245380 | A1 | | 10/2008 | Ecker et al. | |
| 2008/0255527 | A1 | | 10/2008 | Osborne | |
| 2009/0088703 | A1 | | 4/2009 | Azar | |
| 2009/0320868 | A1 | | 12/2009 | Wang et al. | |
| 2010/0087790 | A1 | | 4/2010 | Hurwitz | |
| 2010/0175696 | A1 | * | 7/2010 | Ishizeki | A61M 35/003 128/203.15 |
| 2010/0316430 | A9 | * | 12/2010 | Cable, Jr. | A61M 35/003 401/134 |
| 2011/0092922 | A1 | * | 4/2011 | Trompen | A01K 13/003 604/290 |

* cited by examiner 104
100
102
106

Fig. 4A
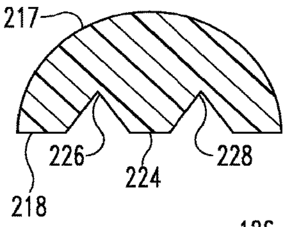
Fig. 5A
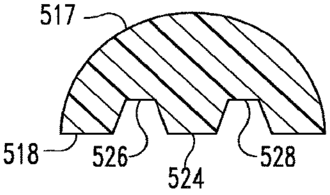
Fig. 7A
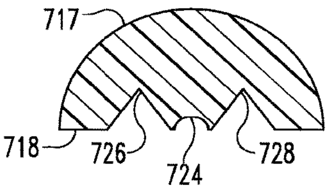
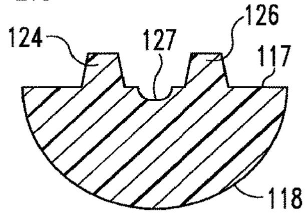
Fig. 4B
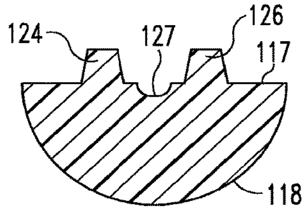
Fig. 5B
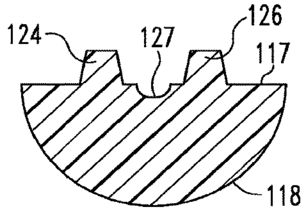
Fig. 7B
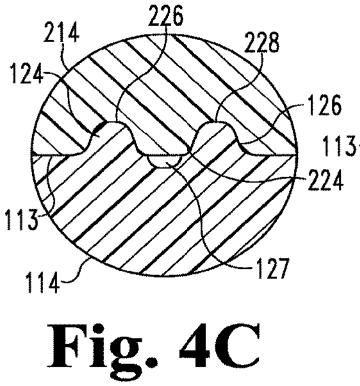
Fig. 4C
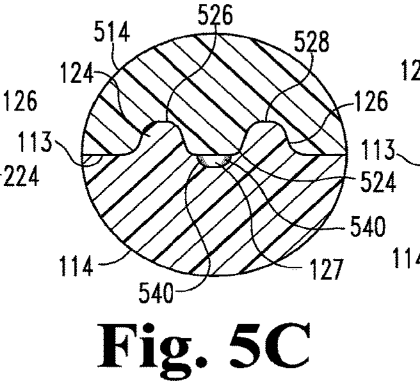
Fig. 5C
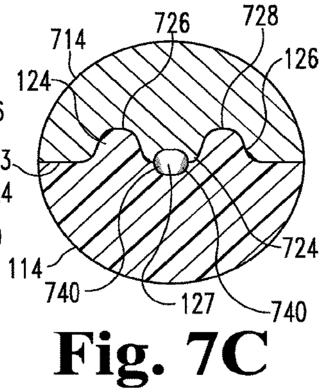
Fig. 7C

TRANSDERMAL DISPENSING APPARATUS AND METHODS

RELATED APPLICATION

This application is a continuation of U.S. patent application Ser. No. 12/581,658 filed Oct. 10, 2009, the entire disclosure of which is incorporated herein by reference.

FIELD OF THE INVENTION

The present invention relates generally to apparatuses and methods for dispensing therapeutic agents to animals, and particularly applicators and methods for transdermally administering therapeutic agents to domestic animals.

BACKGROUND

Drug delivery devices and applicators for dispensing known quantities of therapeutic agents to animals are well known in the art. While there are numerous ways to deliver these therapeutic agents to the coats and skins of the animals, many of these methods are either ineffective and/or present safety risks to the animal or user during or after the dispensing activity. More particularly, because a physical connection must be achieved between the applicator tip and the drug delivery device during the dispensing activity, there is inherently a risk that the connection will be inadequate, thereby permitting some of the therapeutic agent to leak out of the device and into physical contact with the user. Not only is this leakage wasteful and messy, it also places the user at a heightened risk of suffering from a skin irritation or other such health concern, particularly if the user comes into direct contact with the agent. These health and safety risks can be of particular concern when a controlled substance is used as the dispensing agent.

In addition to leakage concerns, many conventional drug delivery devices also have a tendency to leave some residual therapeutic agent inside the body of the device after dispensing is completed. This is not only wasteful both in terms of product and cost, but also presents an increased safety risk to any individual who may contact the device after it has been used. More particularly, if the device still contains a poisonous or skin irritating ingredient, a person may suffer a serious health risk (or even death) if they handle the component after it has been discarded. Further, a residual amount of a controlled substance remaining in the dispenser after dispensing may create an issue of unauthorized use of a controlled substance.

SUMMARY OF THE INVENTION

The present invention overcomes or ameliorates at least one of the prior art disadvantages or provides a useful alternative thereto by providing an apparatus and associated methods for dispensing therapeutic agents, and particularly applicators and methods for transdermally administering therapeutic agents to domestic animals.

In accordance with one aspect of the present invention, an applicator for dispensing a therapeutic agent to an animal is provided. The applicator comprises a housing including first and second sections coupled together, the first and second sections defining a channel therebetween that includes at least one outlet; a hub integral with the first section and extending therefrom, the hub defining a conduit; and a bent path connecting the conduit to the channel. In accordance with this embodiment, the conduit, the bent path and the channel are fluidly connected.

In accordance with yet another aspect of the present invention, a method of manufacturing an applicator for transdermally dispensing a therapeutic agent to an animal is provided. The method comprises providing a first housing section including a hub portion attachable to a syringe and a pair of spaced ribs with a groove formed therebetween, the hub portion further defining a conduit; providing a second housing section including a ledge, the ledge being formed by a pair of spaced grooves; mating the pair of spaced ribs with the pair of spaced grooves to form a channel for dispensing the therapeutic agent, the channel being fluidly connected to the conduit by way of a bent path; and coupling the first housing section to the second housing section to form an applicator body, the applicator body defining at least one outlet for dispensing the therapeutic agent.

In accordance with still another aspect of the present invention, a method is provided for dispensing a therapeutic agent from an applicator of the type having a housing including first and second sections coupled together to form a channel and a hub extending from the housing, the hub being attachable to a syringe. The method comprises attaching the hub to a syringe containing a therapeutic agent; placing an outlet of the applicator on or near the animal; causing the therapeutic agent to be released from the syringe into the applicator; passing the therapeutic agent through the hub, through a bent path and then into the channel; and dispensing the therapeutic agent from the applicator through the outlet.

BRIEF DESCRIPTION OF DRAWINGS

The above-mentioned aspects of the present teachings and the manner of obtaining them will become more apparent and the teachings will be better understood by reference to the following description of the embodiments taken in conjunction with the accompanying drawings, wherein:

FIG. 4A is a cross-sectional view of the top section of an applicator of FIG. 5 taken along line 5A;

FIG. 4B is a cross-sectional view of the bottom section of an applicator of FIG. 4 taken along line 4B;

FIG. 4C is a cross-sectional view of the assembled applicator of FIG. 2 taken along line 4C;

FIG. 5A is a cross-sectional view of a different embodiment of a top section of an applicator;

FIG. 5B is a cross-sectional view of a different embodiment of a bottom section of an applicator;

FIG. 5C is a cross-sectional view of the assembled applicator after the top section of FIG. 5A is ultrasonically welded with the bottom section of FIG. 5B;

FIG. 7A is a cross-sectional view of another embodiment of a top section of an applicator;

FIG. 7B is a cross-sectional view of another embodiment of a bottom section of an applicator;

FIG. 7C is a cross-sectional view of the assembled applicator after the top section of FIG. 7A is ultrasonically welded with the bottom section of FIG. 7B;

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

The present invention is generally directed to drug delivery devices for dispensing liquid based formulations to animals, particularly domesticated or companion animals such as, but not limited to, dogs, cats, horses and the like. While certainly not intended to be required herein, the present invention is particularly useful for transdermally delivering doses of controlled veterinary substances (e.g., Fentanyl) to the coat and skin of an animal. Moreover, an animal may include a human. As such, it should be understood and appreciated herein that the drug delivery devices, systems and methods of the present invention can also be used with other types of fluids, liquids or gels without straying from the teachings of the present invention. Some non-limiting examples of other such substances envisioned to be useful in accordance with the present teachings include, but are not limited to, therapeutic agents, pesticides, parasiticides, glues, solvents, lubricants, medicaments and the like. For simplicity purposes, the present disclosure will primarily focus on therapeutic agents as the illustrative and non-limiting dispensing substance; however, as is clearly explained above, the teachings of the present invention are not intended to be limited to these therapeutic applications alone.

In certain exemplary embodiments of the present invention, the drug delivery device includes an applicator device or tip that is compatible with a standard luer lock syringe and consists of a housing that allows the formulation to be spread over a large surface area of the animal's skin or coat. To accomplish this, the applicator body includes one or more outlets that are in the form of legs or tines configured to penetrate the fur of the animal and thereby deliver the drug directly to the animal's skin or coat. In certain aspects of the present invention, the outlet(s) further includes a pair of spaced prongs or feet that extend from its distal end, thereby allowing the therapeutic agent to be freely dispensed onto the surface of the animal. More particularly, because the spaced feet extend outwardly from the distal end of applicator, they are the only structural portion of the assembled applicator that directly contact and seal against the surface of the animal. Moreover, since the outlet opening is positioned between the spaced apart prongs and in such a manner that it does not directly contact or seal against the surface of the animal during a dispensing operation, the therapeutic agent is able to be freely dispensed and spread onto the animal without being physically impeded or interrupted.

Figure 1:
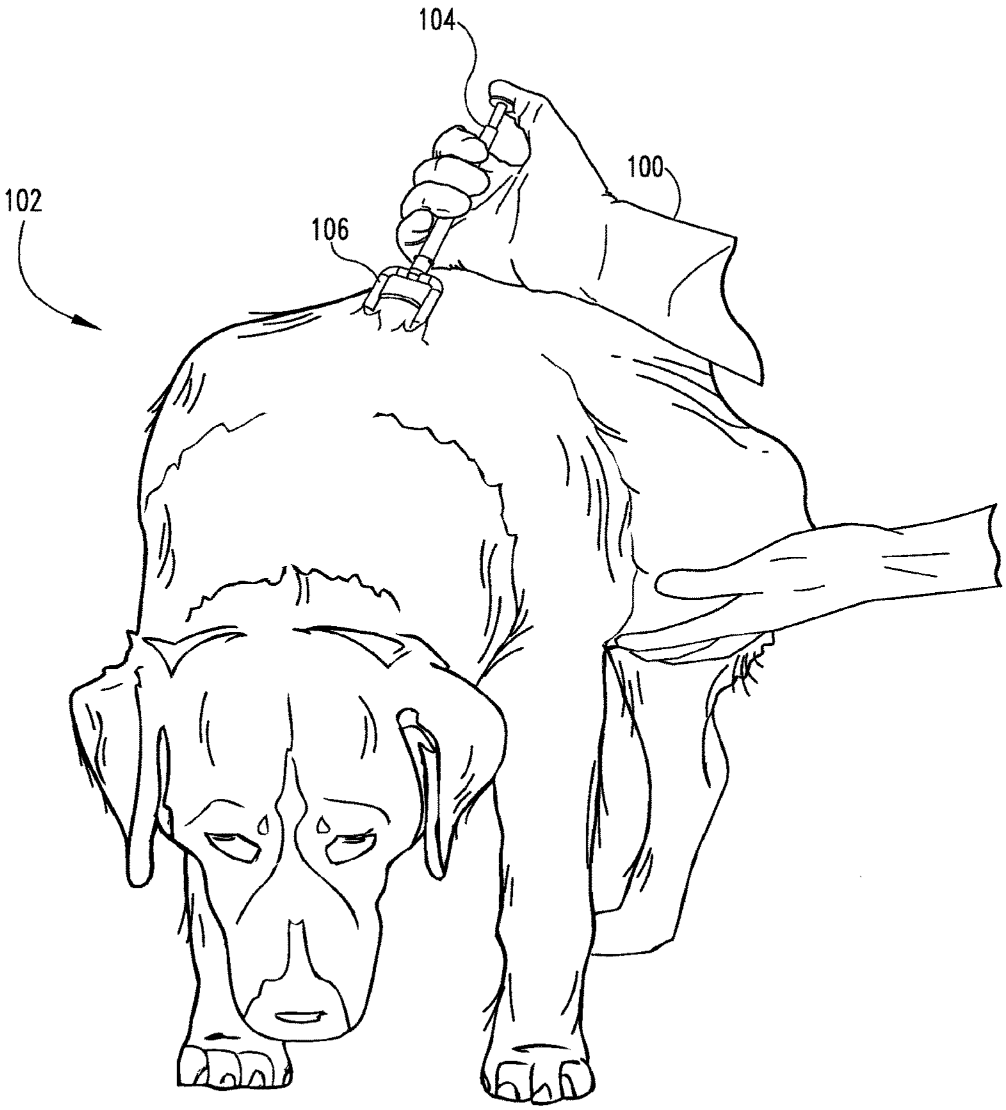
FIG. 1 is a perspective view of an assembled applicator connected to a fluid delivery device and positioned on an animal for dispensing a therapeutic agent onto the animal in accordance with the teachings of the present invention.

A non-limiting illustration of an assembled applicator coupled to a fluid delivery device in accordance with the present teachings is shown in FIG. 1. More specifically, FIG. 1 depicts a perspective view of a user 100 dispensing a therapeutic agent onto an animal 102. In accordance with this exemplary and non-limiting illustration, a fluid delivery device 104 containing therapeutic agent is releasably attached to an applicator device 106 and then placed on or near the surface of the animal 102. While this illustrative embodiment shows the fluid delivery device 104 as a standard syringe, it should be understood and appreciated herein that delivery of the therapeutic agent may be accomplished by any known fluid delivery device or connector that is releasably attachable to the applicator device 106 and having a reservoir for holding and/or storing the therapeutic agent to be dosed or dispensed. Other such non-limiting and illustrative fluid delivery devices that may also be used in accordance with the present invention include, but are not limited to, syringes, catheters, hubbed needles, IV tubes and cylinder fluid delivery devices.

As will be explained in detail below, the applicator devices 106 of the present invention generally consist of at least two parts or halves (i.e., sections 114 and 214) that are coupled or assembled together to form the applicator structure. Unlike many other traditional applicator devices that consist of either one applicator part or two structurally complementary parts, the devices of the present invention include two sections 114, 214 that are somewhat complementary in terms of structure, yet specifically shaped in such a manner that once assembled, the therapeutic agent can be dispensed therefrom without experiencing much associated leakage or residual buildup. More particularly, the sections 114, 214 are structurally shaped such that when they are coupled together, the therapeutic agent is discouraged from leaking out of the applicator body. In addition, the structural orientation of the dispensing passageway that is created between the first and second sections is shaped in such a manner that substantially all of the therapeutic agent is encouraged from being dispensed from the applicator device during a dispensing operation. As such, it should be understood and appreciated herein that at least some of the unexpected advantages of the present invention are influenced by the resultant shape and configuration of the dispensing passageway that is formed by the assembled applicator sections. Additional details of these advantageous characteristics of the present invention are discussed below.

Figure 2:
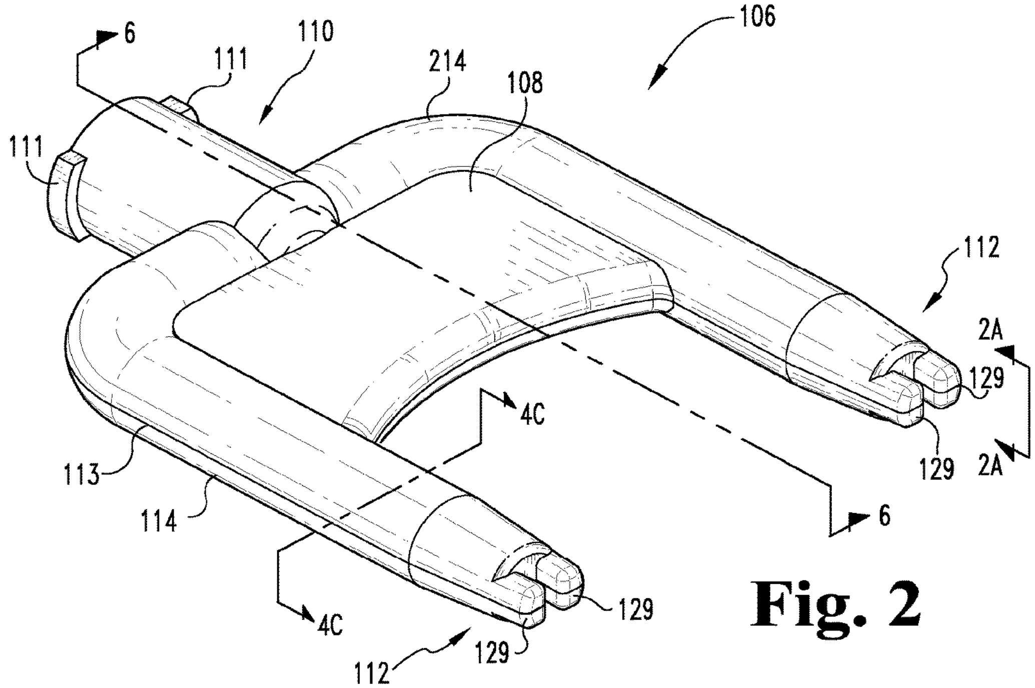
FIG. 2 is a perspective view an assembled applicator in accordance with the present invention.

Moving now to FIG. 2 a perspective view of a fully assembled applicator 106 in accordance with the present invention is shown. The applicator 106 includes a housing or body 108 defining an inlet hub 110 and an outlet 112. As will be explained in more detail below, the inlet hub 110 is attachable to the drug delivery device 104 during a dispensing operation, whereas the outlet portion 112 is capable of penetrating the fur of an animal so that the therapeutic agent can be appropriately dispensed therefrom and onto the surface of the animal. The applicator 106 can be made from polyethylene, polypropylene, polyvinyl acetate, polystyrene, polyethylene terephthalate, polybutylene terephthalate, and polytetrafluoroethylene, and the like.

Figure 3:
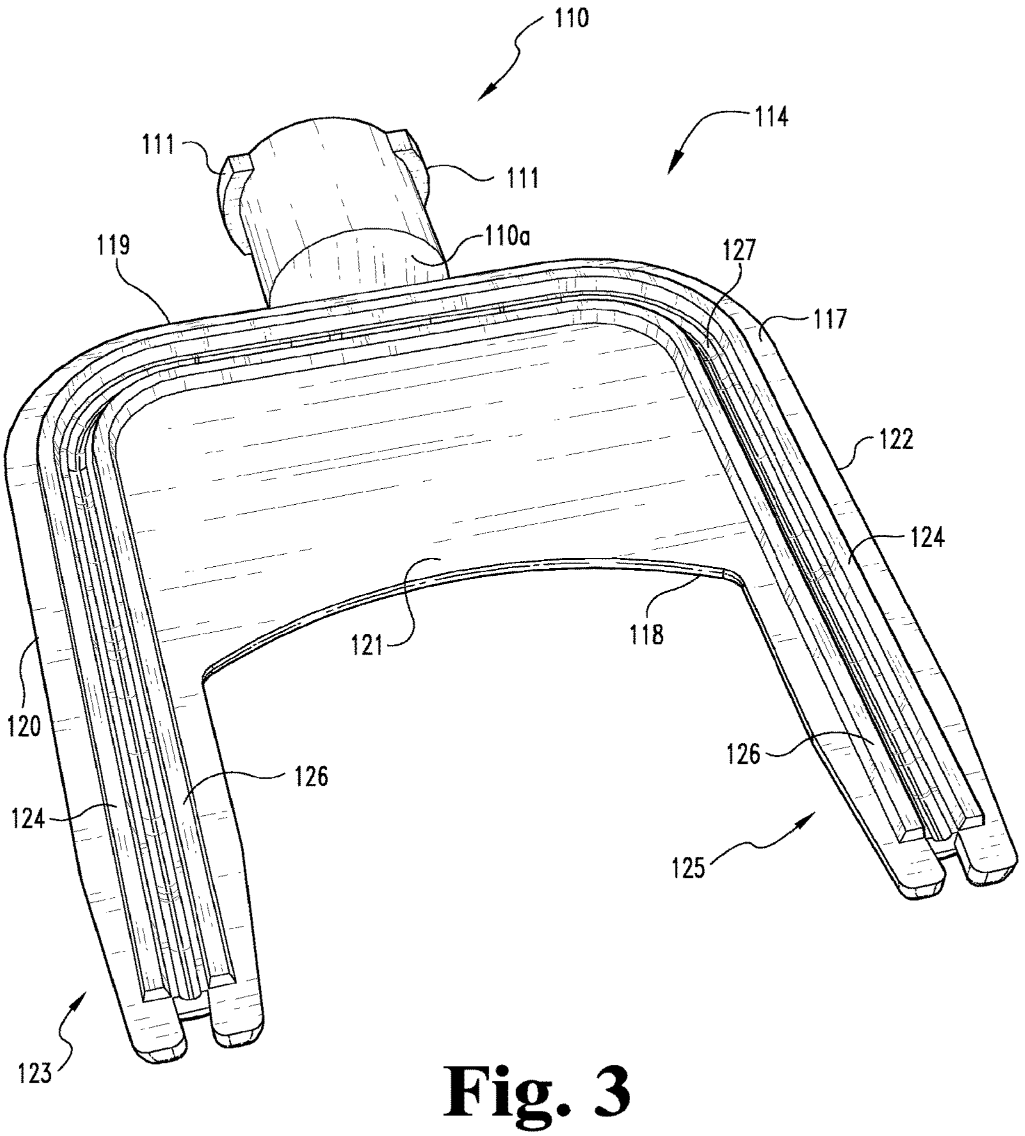
FIG. 3 is a perspective view of the bottom section of an applicator in accordance with the present invention.
Figure 4:
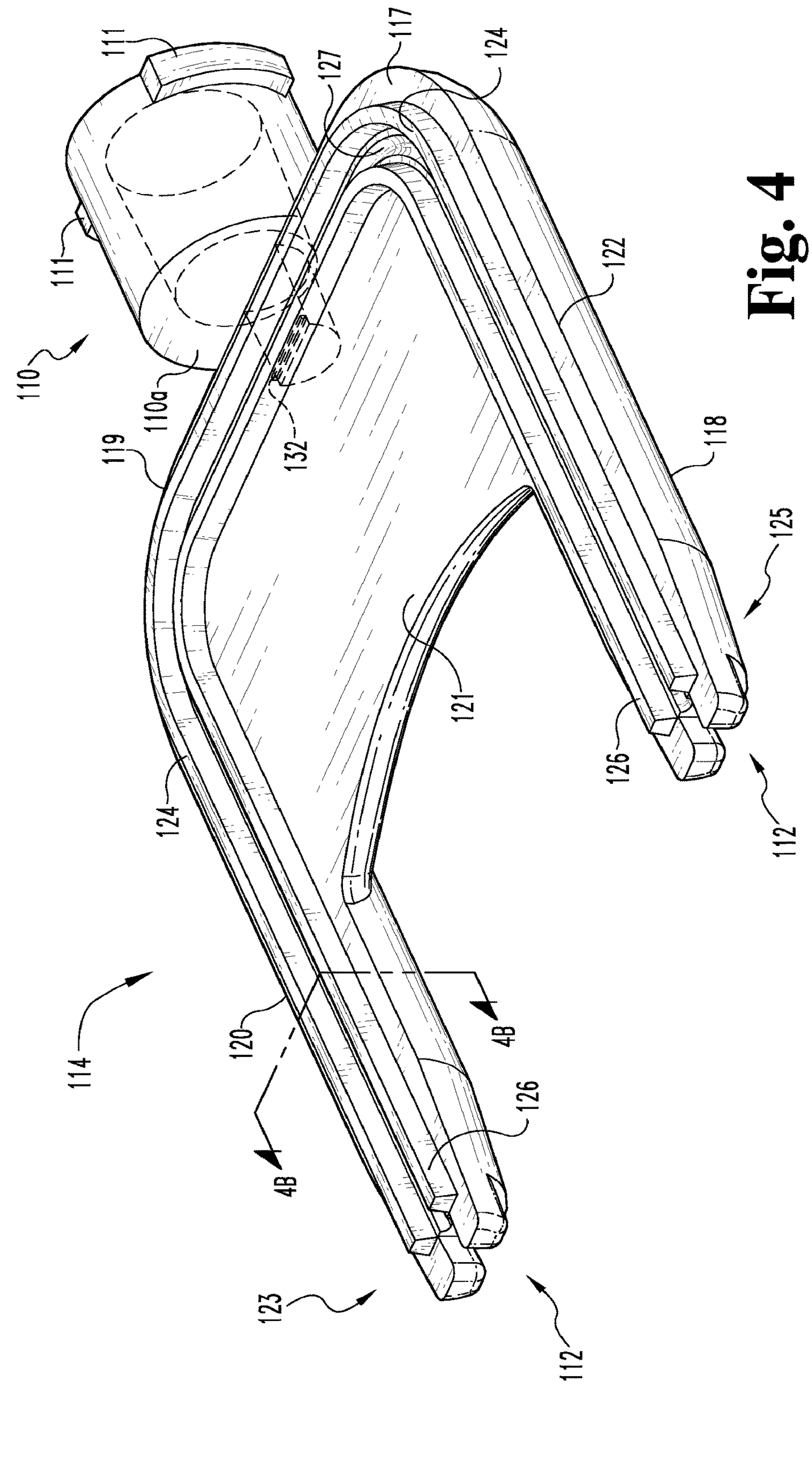
FIG. 4 is another perspective view of the bottom section of an applicator in accordance with the present invention.

In terms of assembly, the applicator 106 comprises first and second sections 114 and 214, respectively, that are coupled or assembled together to form the housing 108. As shown in FIGS. 3 and 4, the first section 114 includes the entirety of the inlet hub 110, a top surface 117, a bottom surface 118, a back edge 119 integral with the inlet hub 110 and first and second sides 120, 122, the first and second sides being defined by a pair of substantially parallel outlet ends or legs 123, 125 that extend from and partially surround a substantially flat middle section 121 that is disposed between the first and second sides 120, 122. Extending upwardly from the top surface 117 of the first preassembled section 114 and positioned substantially along its outer periphery are a pair of ribs 124, 126 that are spaced from each other in a parallel fashion. In certain exemplary embodiments, the ribs 124, 126 are trapezoidal shaped and have four sides with the top and bottom sides being parallel to one another. In accordance with this exemplary embodiment, the spaced ribs 124, 126 have a groove or channel 127 that is formed therebetween.

In certain aspects of the present invention, the groove 127 is sunken or depressed below the top surface 117 of the first section, thereby creating a channel for delivering the therapeutic agent to the outlet ends 123, 125 and ultimately onto the animal. To achieve the sunken channel formation, the groove 127 is provided as a depression below the surface 117 and has a substantially semi-circular shape. A more detailed and non-limiting exemplary illustration of this semi-circular geometry can be seen with reference to FIG. 4B, which illustrates a cross-sectional view of the first section 114 taken along line 4B of FIG. 4. While this exemplary illustration shows the groove or channel 127 being semi-circular in shape, it should be understood and appreciated herein that any known geometric shape useful for establishing a channel that permits a fluid or other such liquid agent to travel therethrough is envisioned and can be used in accordance with the teachings of the present invention. As such, the teachings of the present invention are not intended to be limited herein.

As explained above, it should be understood and appreciated herein that the first preassembled section 114 is configured to be coupled to and melded with the second preassembled section 214 to form a fully assembled applicator device 106. In addition, the channel or groove 127 that is formed between the ribs 124 and 126 is positioned and shaped in such a manner that a fluid passageway or conduit for dispensing the therapeutic agent is formed between the fluid delivery device 104 and the dispensing end of the outlet 112 once section 114 is coupled to and melded with section 214.

Figure 5:
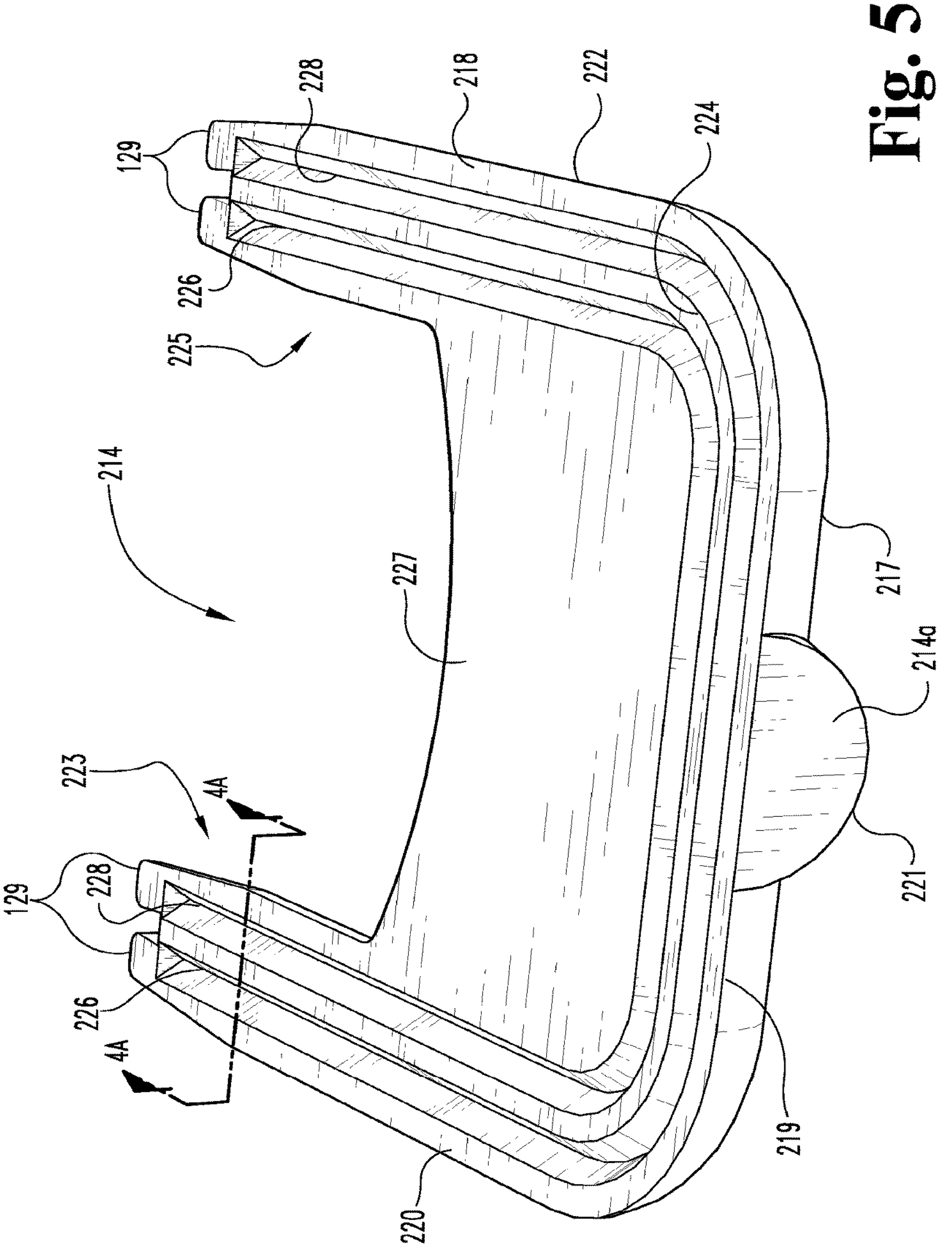
FIG. 5 is a perspective view of the top section of an applicator in accordance with the present invention.

Moving now to FIG. 5, the second preassembled section 214 has a shape that is substantially similar to and which complements the first preassembled section 114; however, it does not have a corresponding inlet hub portion or a rib and groove arrangement like that of the first section 114. Instead, the second section 214 includes a top surface 217, a bottom surface 218, and a back edge 219 having a rounded portion 221 that is substantially centrally located along the back edge 219 and is configured to substantially align with the inlet hub 110 portion of the first section during assembly. To achieve this alignment, the inlet hub 110 has a flat end portion 110*a* that is complementarily shaped to and configured to mate with a flat end portion 214*a* of the second section 214. The second preassembled section 214 also includes first and second sides 220, 222 that are defined by a pair of substantially parallel outlet ends or legs 223, 225 that extend from and partially surround a substantially flat middle section 227 that is disposed between the first and second sides 220, 222. Extending outwardly from the bottom surface 218 of the second section and positioned substantially along its outer periphery is a ledge or energy director 224 that is formed by a pair of spaced grooves 226, 228. A more detailed and non-limiting exemplary illustration of this geometric configuration can be seen with reference to FIG. 4A, which illustrates a cross-sectional view of the second section 214 taken along line 4A of FIG. 5.

During assembly of the applicator 106, the pair of spaced ribs 124, 126 of the first preassembled section 114 are configured to substantially align with (and mate) the spaced grooves 226, 228 of the second section 214, thereby forming the passageway or channel 127 for dispensing the therapeutic agent. In accordance with certain exemplary embodiments of the present invention, the passageway 127 is asymmetric relative to a seamless joint 113 that attaches the first and second sections 114, 214 together. A fully assembled view of the first and second sections 114, 214 aligned and mated together can be seen in FIGS. 4C and 6, which respectively depict a cross-sectional view of the assembled applicator 106 from FIG. 2 taken along line 4C and a cross-sectional side view of the assembled applicator 106 from FIG. 2 taken along line 6.

Figure 2A:
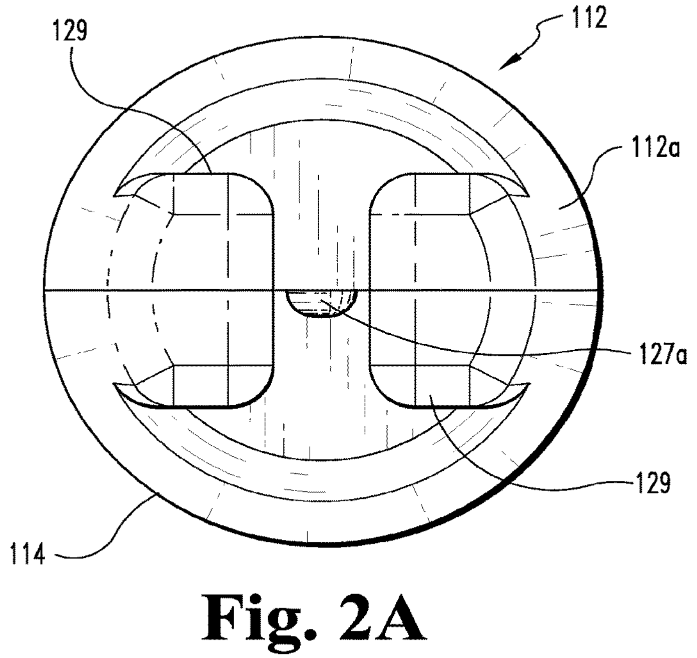
FIG. 2A is an end view of an outlet from the assembled applicator of FIG. 2 taken along line 2A.

As can be seen particularly in FIG. 4C, after the first and second sections are welded together, the spaced ribs 124, 126 meld into grooves 226, 228 so that a seamless joint 113 is formed between the two faces 117, 218, and the channel 127 is formed therebetween. In particular, a substantially flat portion of the channel 127 is defined by a portion of the ledge 224. Once fully assembled, the channel 127 creates a fluid passageway between the inlet hub 110 and the one or more outlets 112. As shown in FIG. 2A, the distal end 112*a* of the applicator's outlet is open (see reference numeral 127*a*) so the therapeutic agent can be emptied from channel 127 during a dispensing application.

In accordance with the teachings of the present invention, the first and second preassembled sections 114, 214 can be coupled together to form an assembled applicator 106 by various known plastic molding and manufacturing methods. However, in certain aspects of the present invention, the applicator 106 is formed by ultrasonically welding the first and second preassembled sections 114, 214 together. In accordance with this exemplary and non-limiting embodiment, the first and second preassembled sections 114, 214 are mated and aligned together as explained above, and an ultrasonic weld, for instance along the ledge 224, is initiated to thereby cause the sections to seamlessly meld or join together. As is readily known and appreciated by those of skill in the plastics manufacturing and welding arts, the process of ultrasonically welding two plastic parts together along an energy director that has been formed into one of the preassembled parts allows a bond to be formed that is tensile and resists the tendency of forces to tear the bond apart. Specifically, the ultrasonic energy melts the point contact between the parts, thereby creating a seamless joint. Moreover, these types of welds can typically be strengthened by either increasing the weld depth, or increasing the size of the energy director to provide a larger weld area. Accordingly, it should be understood and appreciated herein that the precise shapes and sizes of the preassembled components described herein are not essential to the present invention, particularly as a skilled artisan would understand how to maximize the size and shapes of the components to achieve the best welded result for the specific dispensing applicator device to be assembled.

There are, however, advantages to the embodiment of the applicator 106 illustrated in FIGS. 4A, 4B, and 4C. In particular, the structure of the first section 114 and second section 214 is advantageous in forming a substantially semi-circular channel 127 that encourages a therapeutic agent to be dispensed therethrough while leaving only a minimal amount of residual remaining in the channel after use. One reason for this is because the weld path, i.e., seamless joint 113, is disposed close to the fluid path, i.e., channel 127. Another reason is because the channel 127 has a substantially flat portion, the ribs 124, 126 can be positioned closer to one another. As such, the channel 127 can be smaller thereby reducing the overall volume of the channel, which effectively reduces the amount of residual therapeutic agent remaining in the channel after dispensing the agent therethrough.

Another advantage with the illustrated embodiment of the applicator 106 is the shape of the grooves 226, 228 and the ledge 224 in the second section 214. Each groove is substantially V-shaped and the ledge 224 is substantially flat, as shown in FIG. 4A, such that when the first and second preassembled sections 114, 214 are mated and aligned together there is very little, if any, flash remaining in the channel 127. During ultrasonic welding, for example, the ultrasonic energy melts the energy director, i.e., ledge 224, to form the joint 113 between the first and second sections 114, 214. In FIG. 4C, after the first section 114 and second section 214 are welded together, the channel 127 is formed without flash forming in the channel. Flash can disrupt or obstruct the flow of the therapeutic agent passing through the channel 127. Larger amounts of residual fluid can remain in the channel after the therapeutic agent is dispensed when flash is present in the channel 127. By reducing or eliminating flash, the channel 127 maintains a substantially semi-circular shape therethrough, which as described above reduces the amount of residual therapeutic agent remaining in the channel after use.

This is not, however, the case with differently shaped grooves and/or ledge in the second section. In FIG. 5A, for example, a different embodiment of a second section 514 having a top surface 517 and bottom surface 518 is shown. In addition, a different cross-section of the second section 514 is illustrated in which grooves 526, 528 are trapezoidal. The trapezoidal grooves 526, 528 are complementary to the trapezoidal ribs 124, 126 of the first section 114 (FIG. 5B). An energy director or ledge 524 of the second section 514 is substantially flat and therefore similar to the ledge 224 in FIG. 4A. As can be seen in FIG. 5C, after the first and second sections are welded together, the spaced ribs 124, 126 meld into grooves 526, 528 so that a seamless joint 113 is formed between the two faces 117, 518, and the channel 127 is formed therebetween. Unlike the semi-circular channel 127 shown in FIG. 4C, however, the mating of the trapezoidal grooves 526, 528 with the trapezoidal ribs 124, 126 produces flash 540 which fills a portion of the channel 127. The flash 540 reduces the size of the channel 127 such that the channel 127 no longer is semi-circular. One reason flash is produced in the channel is due to the difficulty of welding the trapezoidal grooves 526, 528 and the trapezoidal ribs 124, 126.

In FIG. 7A, another embodiment of a second section 714 having a top surface 717 and bottom surface 718 is shown. Moreover, the second section 714 includes grooves 726, 728 which are V-shaped and therefore similar to the grooves 226, 228 of FIG. 4A. The second section 714, however, also includes an energy director or ledge 724 that is not flat. Instead, the ledge 724 is pressed above the bottom surface 718 and has a semi-circular cross-section. The shape of the ledge 724 complementarily corresponds with the semi-circular channel 127 of the first section 114 shown in FIG. 7B. As can be seen in FIG. 7C, as the first and second sections are welded together, the spaced ribs 124, 126 meld into grooves 726, 728 so that a seamless joint 113 is formed between the two faces 117, 718, and the channel is formed therebetween. The channel 127 formed between the first and second sections has a substantially circular cross-section, but flash 740 forms in the channel thereby inhibiting flow therethrough. Flash is produced in the channel 127 due to the difficulty of welding the two sections together. As can be seen in FIG. 7A, for example, the ledge 724 is no longer substantially flat. In particular, there is very little material along the ledge 724 that contacts the first section 114 for ultrasonically welding the two sections together. Thus, to ensure a proper bond is formed to hold the first and second sections together, flash fills along the edges of the channel 127. Therefore, while it should be understood and appreciated herein that the precise shapes and sizes of the preassembled components described herein are not essential to the present invention, it is advantageous for the preassembled components to comprise shapes and sizes that facilitate little to no flash.

A more detailed description of the various parts of the applicator 106 will now be provided. As is particularly shown in FIGS. 6, 8, 8A and 8B, the hollow inlet hub 110 is integral with the first section 114. The interior surface of the hollow inlet hub 110 defines and is fluidly connected to the groove or channel 127 by way of a path defined by a jointless and therefore seamless conduit that extends between a pair of openings 130, 132. As should be understood and appreciated herein, the fluid connection provided by the conduit between the interior of the hollow inlet hub 110 and the channel 127 defines a jointless, and thus a seamless, flow path for the therapeutic agent from the fluid delivery device 104 to the groove or channel 127. More particularly, the inlet hub 110 has a first, inlet opening 130 that is disposed at the proximal end 211 of the inlet hub 110 and functions as an insertion hole for receiving the dispensing end of the fluid delivery device (such as device 104 in FIG. 1). Opposite the first opening 130, the inlet hub conduit has a second opening 132, which is fluidly connected to the groove or channel 127 of the housing 108. As such, the inlet hub 110 is designed to functionally form an opening for the fluid delivery device 104 so that the therapeutic agent can be easily and conveniently dispensed therefrom.

The inlet hub 110 has a pair of winged ears 111 adapted to lock to the fluid delivery device (not shown). More particularly, the fluid delivery device (e.g., device 104 in FIG. 1) is inserted into first opening 130 and securely attached to inlet hub 110 by any fastening means known in the art. Exemplary connection means in accordance with the present invention include, but are not limited to, luer lock connections. Luer lock connections are well known in the field of medicine and are typically used for coupling a syringe or other such liquid or gas source to a catheter line or medical device. Moreover, as will be appreciated and understood by those skilled within the relevant art, the luer connectors of the present invention may be female or male in orientation and may function as luer-locking devices, luer-slip connection devices or the like. In accordance with specific aspects of the present invention, the luer lock connection is achieved between the fluid delivery device 104 and the winged ears 111 of the inlet hub 110.

Figure 6:
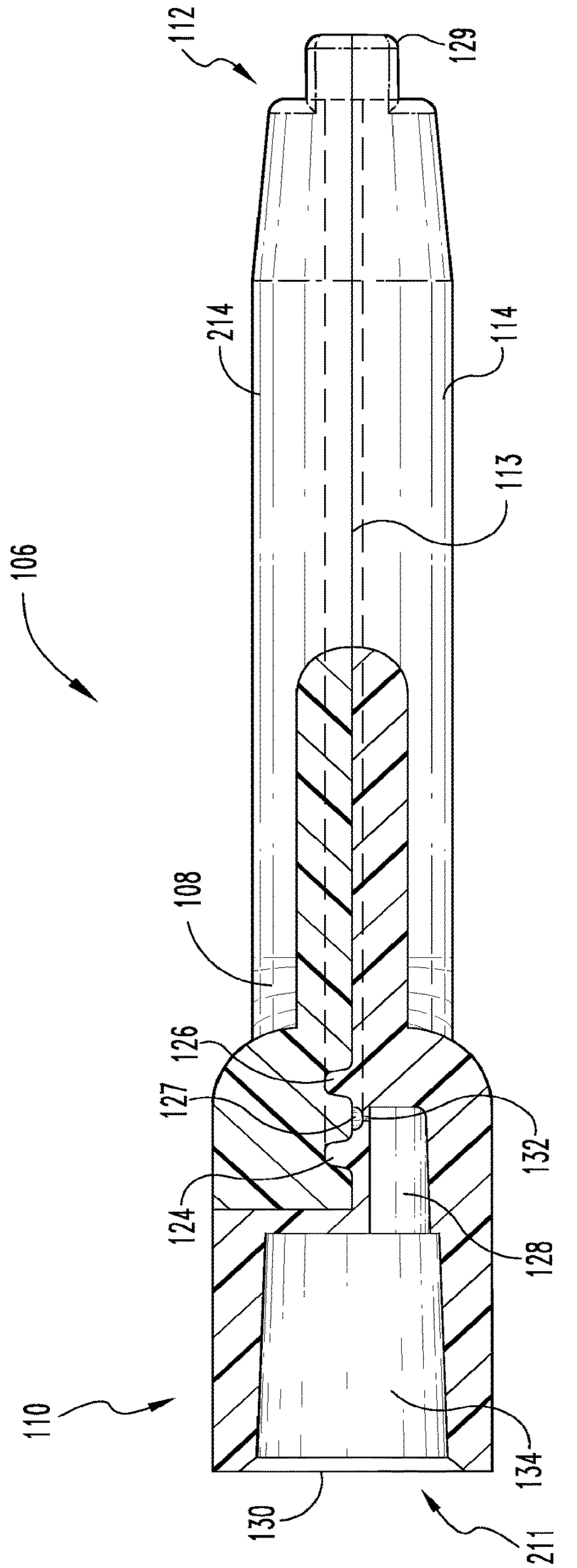
FIG. 6 is a cross-sectional side view of an assembled applicator of FIG. 2 taken along line 6.
Figure 8A:
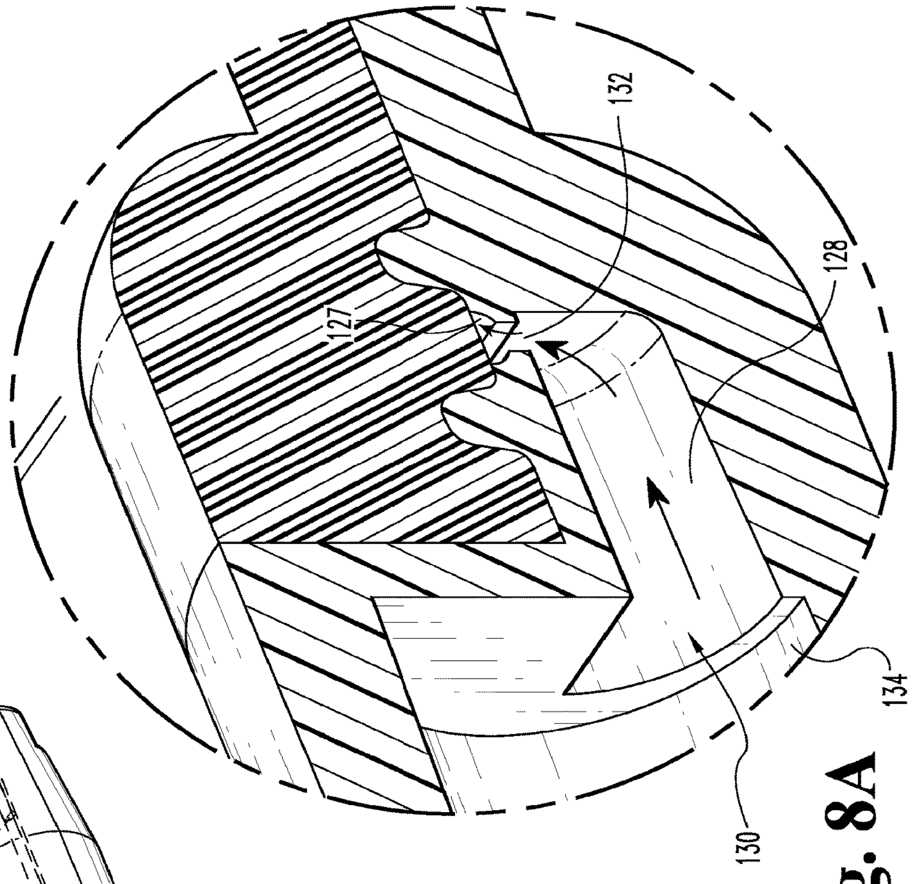
FIG. 8A is a magnified cross-sectional view of a portion of the assembled applicator of FIG. 8 and indicated by circle 8A.
Figure 8:
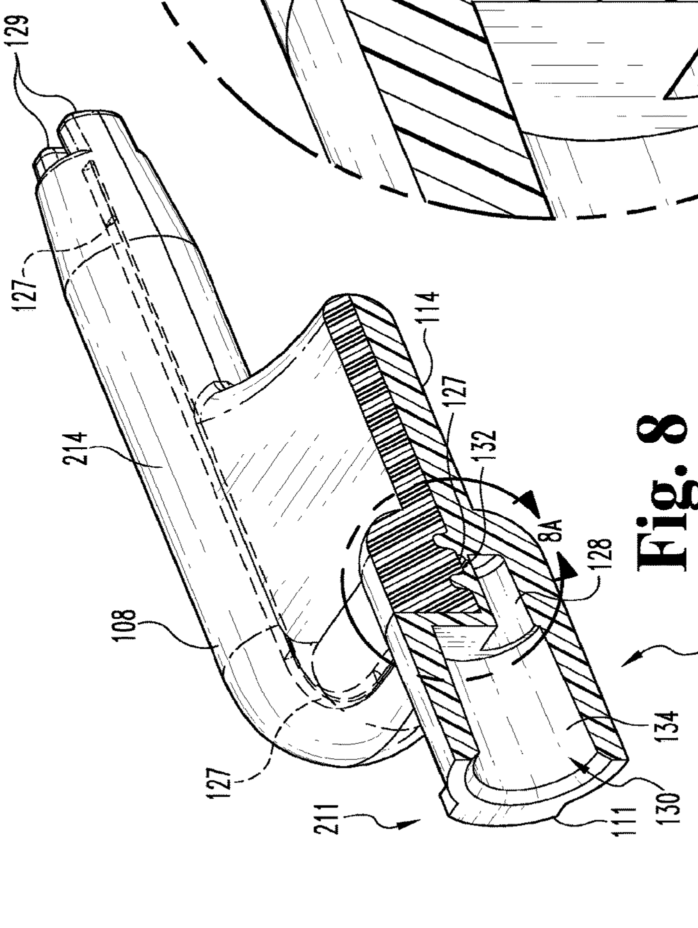
FIG. 8 is a cross-sectional view of an assembled applicator in accordance with the present invention.
Figure 8B:
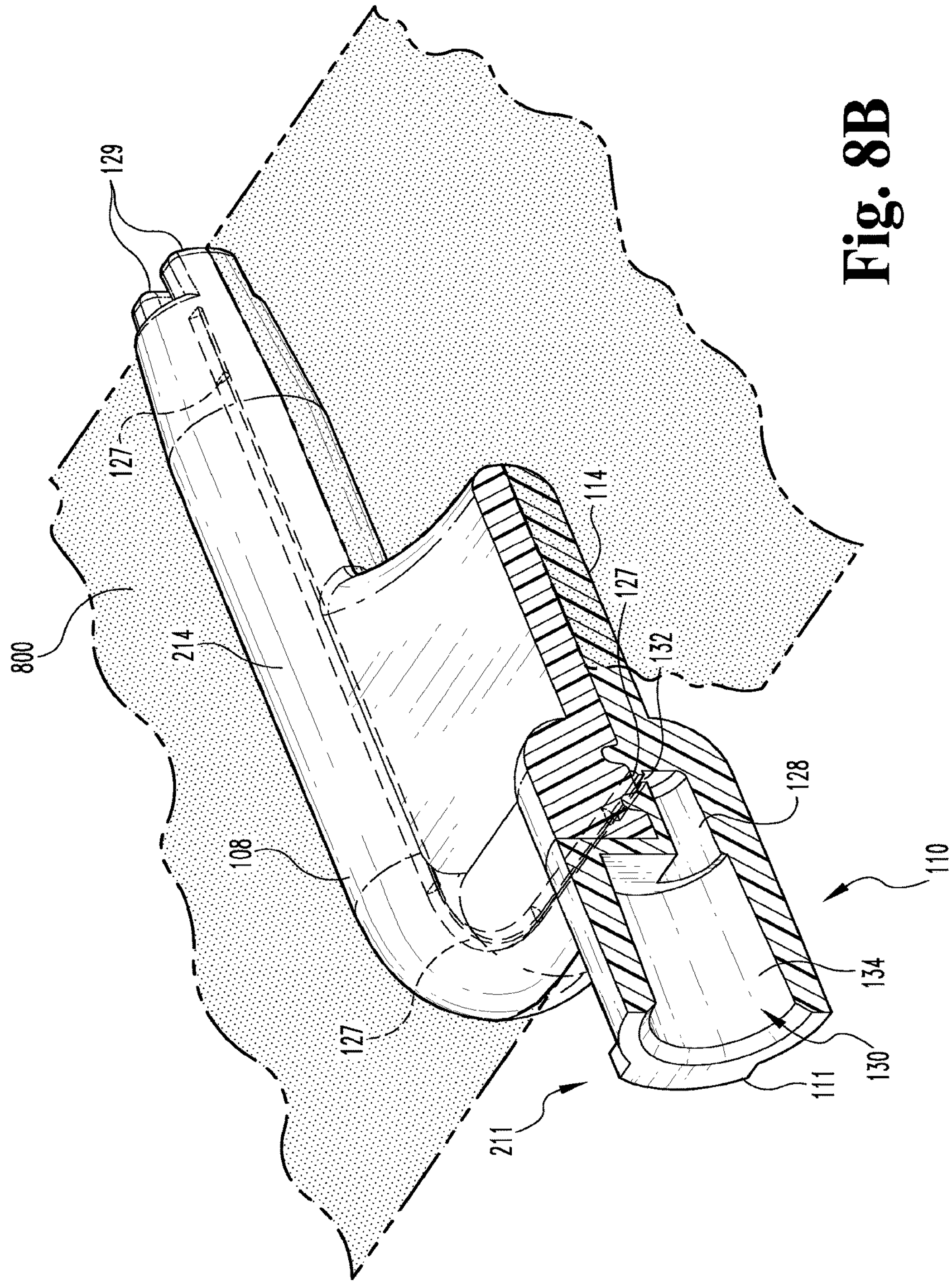
FIG. 8B is a cross-sectional view of the assembled applicator of FIG. 8 showing a plane passing through the joint.

As can be appreciated from the discussion above and clearly shown in FIGS. 6, 8, and 8A, the inlet hub conduit undergoes a significant reduction in size along its flow path in the direction of fluid flow (i.e., in the direction from the inlet hub 110 to the distal end 112*a* of the outlet 112). This is necessary to adapt the applicator for connection to larger fluid delivery devices at the proximal end 211 of hub 110 on the one hand and, on the other hand, introducing the fluid delivered into the conduit to the very small channel 127 through which the fluid is moved before being dispensed from the outlet(s) 112. This reduction in conduit size causes significant pressure within the inlet hub conduit, which in turn can cause leakage if there are any weak or vulnerable points such as weld joints along the path. To address these structural issues, the flow path along the conduit is bent or shaped such that it is circuitous in nature—i.e., is not a direct route between the first and second openings 130, 132 and changes direction one or more times. In this manner, the inlet hub conduit is formed entirely within a single section, section 114, of the applicator, which avoids weld joints being present for any of the structure that defines the flow path. With reference to FIG. 8B, for example, the interface between the first and second sections, i.e., joint 113 (FIG. 2), defines a plane 800 that passes therethrough. As shown in this illustrative embodiment, the flow path along the conduit is offset from the plane 800. By locating the flow path in one section, i.e., first section 114 of the applicator (as opposed to two sections defining a conduit located therebetween) and consequently eliminating all weld joints along the conduit flow path, the occurrence of leakage of the fluid at locations between the fluid delivery device 104 and the channel 127 is substantially reduced, if not eliminated.

The conduit structure defining the flow path can be appreciated with reference to FIGS. 8 and 8A, wherein the conduit defined by the inlet hub 110 includes a short, hollow, substantially cylindrical chamber 134 that is disposed between the first and second openings 130, 132 and terminates substantially centrally into the channel 127 at the second opening 132. As shown, the conduit is typically designed such that it is dimensionally non-uniform (i.e., varies in its cross-section dimensions between the first opening 130 and the second opening 132). According to this aspect of the present invention, the internal dimensions of the conduit change to achieve the reduction in size and the configuration needed to maintain its flow path within a single section 114 of the applicator. As mentioned above, the present inventors have found that this configuration avoids leakage of the therapeutic agent as it flows between the fluid delivery device and the channel.

In certain aspects of the present invention one or more tubes or other such enclosed tubular structures can be internally incorporated into the structural design of the present applicators. For instance, to avoid any associated leakage that may occur around the connection between the fluid delivery device and the applicator or along the joint 113 that is formed between the first and second molded sections 114, 214, one or more chambers can be internally added into the inlet hub 110 portion and/or within the formed channel 127 of the applicator body. While such additional structure can be incorporated into any of the embodiments of the present invention without straying from the present teachings, it should be understood and appreciated herein that such structures are not required. More particularly, the present inventors have found that utilizing the bent path orientation and complementary structural design of the applicator sections makes it possible to achieve a tubeless design that is not only free of manifolds, but is also capable of operating without resultant leakage.

In certain exemplary embodiments in accordance with the present invention, the conduit contains ridges, ledges, or other such similar structures to cause a bending configuration and stepped down size relative to that of its chamber 134. In still other aspects of the present invention, the conduit path is positioned below the seamless joint 113 that is formed between the first and second sections 114, 214 and underneath the channel 127 formed therebetween.

In accordance with certain aspects of the present invention, the second opening 132 directs the therapeutic agent into the channel 127 in a direction that is substantially orthogonal to the lengthwise direction of the channel 127. Such exemplary embodiment can be seen, for instance, with reference to FIGS. 8 and 8A. While the dimensions and/or geometric shape of the second opening 132 can be adjusted to fit a specific drug delivery application, in accordance with certain aspects of the present invention, the opening 132 is substantially rectangular in shape.

In accordance with yet another illustrative aspect of the present invention, a portion of the bent path extends through a conduit portion 128 having a substantially semi-circular cross-section. The semi-cylindrical conduit portion 128 is connected to the chamber 134 for receiving the therapeutic agent from the fluid delivery device 104 and conducting it to the channel 127. In accordance with this illustrative aspect, the bent path defined by the conduit terminates at the second opening 132, which in turn, is positioned substantially orthogonally relative to the substantially semi-cylindrical conduit portion 128.

Once the therapeutic agent completely travels and circumnavigates the channel 127 and reaches the distal end 112*a* of the one or more outlets 112, it is now ready to be dispensed onto the surface or coat of the animal. As explained above, to spread the formulation evenly over a large surface area of the animal, the outlet 112 must be able to penetrate the animal's fur and thereby reach the animal's skin. To accomplish this, the outlet 112 may include one or more prongs 129 for assisting with the dispensing of the therapeutic agent onto the surface of the animal. In accordance with certain exemplary embodiments, the prongs 129 comprise spaced feet or tines that are configured to penetrate the fur of the animal 102 so that the applicator 106 can substantially reach or touch the surface of the animal's body during the dispensing of the therapeutic agent. This penetration allows a more efficient topical and transdermal release of the agent. In addition, those of skill in the drug delivery and fluid dispensing arts will understand and appreciate that the addition of prongs or other such structural projections from the outlet 112 will discourage capillary action or attraction (i.e., will stop the therapeutic agent from moving upwardly along the outside of the outlet) from happening during the dispensing action. The minimization and/or elimination of such capillary action effects are particularly beneficial when dealing with therapeutic agents that can be considered harmful and/or dangerous.

While various illustrative embodiments incorporating the principles of the present teachings have been disclosed hereinabove, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain and which fall within the limits of the appended claims.

What is claimed is:

1. An applicator for dispensing a therapeutic agent from a fluid delivery device to an animal, the applicator comprising:

a first section including an inlet hub and a fluid path in fluid communication with the inlet hub, the inlet hub comprising a chamber adapted to receive at least a portion of the fluid delivery device, and the fluid path having an inlet opening in fluid communication with the chamber and an outlet opening, the first section further including one of two planar surfaces;

a second section coupled to the first section and forming a channel therebetween having at least one outlet, the second section including the other of the two planar surfaces;

the two planar surfaces in contact with each other and defining a plane therebetween;

a pair of spaced ribs extending outwardly from one of the two planar surfaces;

a pair of spaced grooves extending inwardly from the other of the two planar surfaces, the pair of spaced ribs mated with the pair of spaced grooves from the outlet opening of the fluid path to the at least one outlet of the channel to form the channel therebetween, the chamber, the fluid path, and the channel fluidly coupled to enable flow of the therapeutic agent from the fluid delivery device through the at least one outlet to the animal.

2. The applicator of claim 1, wherein a cross-sectional area of the fluid path perpendicular to a length thereof is smaller than a cross-sectional area of the chamber perpendicular to a length thereof, creating a higher pressure within the fluid path than within the chamber when therapeutic agent is dispensed from the fluid delivery device, and wherein the pair of spaced ribs and the pair of spaced grooves are shaped to dispense the therapeutic agent through the channel substantially without leakage.

3. The applicator of claim 1, further comprising at least one prong located proximate the at least one outlet, the at least one prong extending distally from the at least one outlet to enable free-flow of the therapeutic agent while the prong contacts the animal.

4. The applicator of claim 3, wherein the at least one prong comprises one of a pair of spaced tines and a pair of spaced feet.

5. The applicator of claim 1, wherein the fluid path is seamless.

6. The applicator of claim 1, wherein the fluid path comprises a semi-cylindrical shape.

7. The applicator of claim 1, wherein the channel comprises a semi-circular surface opposite a flat surface.

8. The applicator of claim 1, wherein the inlet hub further comprises a luer connector for attachment to the fluid delivery device.

9. The applicator of claim 1, wherein the plane intersects the chamber and does not intersect the fluid path.

10. The applicator of claim 1, wherein the fluid path is bent.

11. The applicator of claim 10, wherein the fluid path comprises at least one turn.

12. The applicator of claim 1, wherein a portion of the fluid path is parallel to the plane.

13. The applicator of claim 1, wherein the fluid path is offset from the plane.

14. The applicator of claim 1, further comprising two legs extending along the plane distally of the inlet hub and having distal ends, wherein the at least one outlet comprises a pair of outlets disposed at the distal ends of the two legs, the channel extending through the two legs and terminating at the pair of outlets.

15. The applicator of claim 14, wherein the outlet opening of the fluid path is positioned on a first channel section of the channel intermediate the two legs.

16. The applicator of claim 1, wherein the inlet hub and the fluid path are formed entirely in the first section.

* * * * *

UNITED STATES PATENT AND TRADEMARK OFFICE
CERTIFICATE OF CORRECTION

PATENT NO. : 9,883,932 B2  
APPLICATION NO. : 14/618993  
DATED : February 6, 2018  
INVENTOR(S) : Mick A. Trompen et al.

Page 1 of 1

It is certified that error appears in the above-identified patent and that said Letters Patent is hereby corrected as shown below:

In the Drawings

Sheet 1 of 9, add the label --Fig. 1-- to the drawing.

Signed and Sealed this  
Tenth Day of April, 2018

Andrei Iancu  
*Director of the United States Patent and Trademark Office*